United States Patent [19]

Hazen et al.

[11] Patent Number: 5,238,604
[45] Date of Patent: * Aug. 24, 1993

[54] CROP OIL CONCENTRATES

[75] Inventors: James L. Hazen, Apex; John R. Evans; Edward J. Panek, both of Durham, all of N.C.

[73] Assignee: BASF Corporation, Parsippany, N.J.

[*] Notice: The portion of the term of this patent subsequent to May 30, 2006 has been disclaimed.

[21] Appl. No.: 644,695

[22] Filed: Jan. 22, 1991

Related U.S. Application Data

[63] Continuation of Ser. No. 358,324, May 26, 1989, abandoned, which is a continuation-in-part of Ser. No. 104,658, Oct. 5, 1987, Pat. No. 4,834,908.

[51] Int. Cl.$^5$ .................. B01J 17/44; B01J 17/34
[52] U.S. Cl. .................. 252/356; 71/DIG. 1; 106/250; 106/267; 252/351; 252/354; 252/353
[58] Field of Search .................. 71/DIG. 1, 103; 252/356, 354, 351; 106/250, 267

[56] References Cited

U.S. PATENT DOCUMENTS 4,249,937  1/1981  Iwataki et al. .................. 71/103
4,447,257  5/1984  Gerwick, III .................. 71/DIG. 1
4,834,908  5/1989  Hazen et al. .................. 252/356

FOREIGN PATENT DOCUMENTS 6810762  2/1970  Netherlands .................. 71/DIG. 1

OTHER PUBLICATIONS

McCowan, "Turf Herbicide Rx . . . ", *Agricultural Chem.* (23) 4, Apr. 1968.
Thomson, *Agricultural Chemicals, Book II Herbicides* (1983-1984 edition), 1983, Thomson Pub., pp. 238-239.

*Primary Examiner*—Richard L. Raymond
*Assistant Examiner*—B. M. Burn
*Attorney, Agent, or Firm*—William G. Conger; Karen M. Dellerman

[57] ABSTRACT

Crop oil concentrates are disclosed which increase the herbicidal efficacy of herbicides from diverse chemical classes. These crop oil concentrates comprise an anionic polyoxyalkylene surfactant or salt thereof, an adjuvant which is exclusively a fatty acid or its ester, and a hydrocarbon component. These crop oil concentrates are especially effective with cyclohexenone and triketone herbicides and growth regulators.

5 Claims, No Drawings

CROP OIL CONCENTRATES

This is a continuation of copending application Ser. No. 07/358,324 filed on May 26, 1989, now abandoned, which is a continuation-in-part of Ser. No. 104,658 filed Oct. 5, 1987 now issued as U.S. Pat. No. 4,834,908 on May 30, 1989.

BACKGROUND OF THE INVENTION

1. Field of the Invention

The subject invention relates to crop oil concentrates. More particularly, the subject invention relates to improved crop oil concentrates which enhance the efficacy of herbicides, over and above standard crop oil concentrates which are commercially available.

2. Description of the Related Art

It is well established that a variety of adjuvants play important roles in the application of herbicides. These adjuvants are a diverse group of components with equally diverse functions which may often be determined from their generic names, i.e. "spreaders," "stickers," "solubilizers," "emulsifiers," "flow control agents," "drift control agents," and so on. Among the many useful herbicide adjuvants are the so-called "crop oil concentrates."

Crop oil concentrates are often recommended by herbicide manufacturers and formulators for inclusion in tank mixes to increase the efficacy of postemergent herbicide formulations. Crop oil concentrates are available from a variety of sources, and generally consist of from 75–95 percent by weight of a hydrocarbon oil or solvent with the balance being a surfactant. The hydrocarbons which form the bulk of the crop oil concentrate may be derived from mineral (petroleum) or vegetable sources.

Although the use of selected crop oil concentrates may enhance herbicidal efficacy, it is well known that many of the proprietary concentrates available are not as effective as others. Some may even impact negatively upon herbicidal efficacy. Additionally, there is a great deal of inconsistency with regard to the make up of available crop oil concentrates. Finally, to further complicate the situation, manufacturers frequently change the formulations without notifying the consumer, resulting in a great deal of uncertainty with regard to their performance.

In recent years, the situation with respect to crop oil concentrates has achieved such a level of notoriety that some agriculturists refer to them as "snake oils." Thus there is a need in the agricultural sector, for a crop oil concentrate with a well defined make-up which is capable of enhancing the efficacy of a broad spectrum of herbicides, and which gives reproducible results.

In copending application Ser. No. 104,658 are disclosed crop oil concentrates containing a specific class of anionic polyoxyalkylene surfactants, a long chain fatty acid component, a lower alkanol ester of a fatty acid, and optionally, a hydrocarbon component. These crop oil concentrates were effective adjuvant systems and moreover, decreased the apparent antagonism which occurs when certain herbicides are utilized together in the same tank mix.

SUMMARY OF THE INVENTION

It has now been surprisingly discovered that effective crop oil concentrates may be prepared which are similar to those disclosed in U.S. application Ser. No. 104,658, but which do not contain both the lower alkanol ester of a fatty acid and a fatty acid, but which contain either of these components to the exclusion of the other.

DESCRIPTION OF THE PREFERRED EMBODIMENTS

The crop oil concentrates of the subject invention comprise a mixture of (a) an anionic surfactant derived from esterification of a polyoxyalkylene nonionic surfactant with a dihydric or trihydric inorganic acid or by carboxylation with an organic acid derivative; (b) a long chain carboxylic acid or lower alkanol ester thereof; and (c) a hydrocarbon component.

The anionic surfactants (a) which are useful in the practice of the subject invention are preferably the partial sulfate and phosphate esters of polyoxyalkylene ethers. These partial esters are prepared by methods well known to those skilled in the art, for example by reacting one of the well known and commercially available monohydric polyoxyalkylene ethers with sulfuric acid or phosphoric acid or their chemical equivalents. The sulfate esters so obtained consist predominantly of the half ester (monoester) while the phosphate esters generally contain both mono- and diesters. Also useful, are the carboxylate surfactants, as are also the simple salts of these surfactants, for example, the alkali metal, alkaline earth metal or ammonium salts, particularly the latter.

The methods of preparation of such surfactants are well known to those skilled in the art. The sulfate esters may be prepared, for example, by reacting a suitable mono-functional polyoxyalkylene ether with sulfuric acid or its chemical equivalent, preferably sulfamic acid or sulfur trioxide. The phosphate esters may be prepared similarly by reaction of the monofunctional polyoxyalkylene ether with phosphoric acid, diphosphorus pentoxide, polyphosphoric acid, or phosphorus oxytrichloride. Methods of preparation are described in the treatise *Nonionic Surfactants*, Martin Schick, Ed., Marcel Dekker, New York, ©1967, in Chapter 11, pp 372–394.

The nonionic, monofunctional polyoxyalkylene ethers used to prepare the sulfate and phosphate esters are also well known to those skilled in the art, and are available commercially from many sources. Preferred nonionic, monofunctional polyoxyalkylene ethers have molecular weights of from about 400 to about 3000 Daltons, more preferably from about 600 to about 1200 Daltons, and particularly about 800 Daltons.

The preferred polyethers are prepared by oxyalkylating a monofunctional initiator by known methods. Preferred initiators are the alkylphenols such as octyl- and nonylphenol, and the aliphatic alcohols, particularly the latter. The preferred aliphatic alcohols have from 6 to 30, more preferably from 10 to 20, and in particular, from 12 to 16 carbon atoms in the aliphatic residue.

The alkylene oxides which may be used to prepare the nonionic monofunctional polyoxyalkylene intermediates include ethylene oxide, propylene oxide, and butylene oxide. Tetrahydrofuran may also be useful. Preferred alkylene oxides are ethylene oxide and propylene oxide. When both these oxides are utilized, they may be added simultaneously, in sequence, or in combinations of these modes of addition, to prepare block, heteric, and block-heteric surfactants. Ethylene oxide may also be used alone to form homopolymeric polyoxyethylene polyethers.

The carboxylate surfactants are derived from oxyethylated aliphatic alcohols by reaction with chloroacetic acid in the presence of base. The preparation is described in the Schick treatise, supra, at pages 388–89. Preferably, the aliphatic alcohol contains from 8 to 18, more preferably from 10 to 14 carbon atoms, and is oxyethylated with from 2 to 10, preferably from 3 to 8 moles of ethylene oxide. Preferred is the carboxylate formed from the reaction of chloroacetic acid and the four mole oxyethylate of lauryl alcohol. Reference in the specification and the claims to "carboxylates" of monohydroxyl functional polyoxyalkylene ethers is to this type of surfactant.

Exemplary anionic surfactants include CRODAPHOS® CAP, a product of Croda, Inc., a phosphate ester; SURFINE® WNG-A, a product of Finetex, Inc., a carboxylate ester; ALIPAL® CO-436, a product of GAF Corporation, an ammonium salt of sulfated nonylphenol ethoxylate; ATPHOS® 3220, a product of ICI Americas, Inc., a phosphate ester; and KLEARFAC® AA-270, a product of BASF Corporation, a phosphate ester.

The long chain carboxylic acid (b) (i) may have a chain length, of from 10 to 22 carbon atoms. Preferably, the carboxylic acid is selected from the group of naturally occurring fatty acids such as stearic acid, linoleic acid, linolenic acid, palmitic acid, oleic acid, and the like and mixtures thereof. The unsaturated fatty acids are preferred. Most preferably, the organic acid is oleic acid.

The lower alkanol ester of the long chain carboxylic acid (b) (ii) may be considered as derived from a lower alkanol having from 1 to 4 carbon atoms, such as methyl alcohol, ethyl alcohol, propyl alcohol, or butyl alcohol, and a long chain carboxylic acid. The methyl and ethyl esters are preferred. Most particularly, the methyl esters are utilized. The long chain carboxylic acid generally contains from 10–22 carbon atoms, preferably from 14–18 carbon atoms. Preferred are those carboxylic acids obtainable from natural sources such as fats and oils, for example lauric, myristic, stearic, linoleic, linolenic, palmitic, and oleic acids. Mixtures of these acids are also useful. Preferred are oleic and palmitic acids and their mixtures. Thus the most preferred alkanol esters are methyl oleate, methyl palmitate, and mixtures of these esters. In the remainder of the specification, such compounds will be referred to as lower alkanol esters.

The hydrocarbon component (c) may be derived principally from vegetable or petroleum sources. Hydrocarbon components derived from petroleum sources may be predominantly aliphatic or aromatic. Preferred are the aromatic solvents particularly those containing alkylated benzenes and naphthalenes. Such solvents are readily available from a number of sources, for example, the Shellsolve® solvents, available from the Shell Oil Co., Houston, Tex., and the Aromatic® 150 and 200 solvents available from the Exxon Corporation. The term "hydrocarbon component" as used herein should be taken as including both aliphatic and aromatic solvents as well as their mixtures. The hydrocarbon component is believed to exert some biochemical effect in concert with that of the remaining ingredients, and hence may be considered an active ingredient.

The crop oil concentrates generally contain, in percent by weight relative to the total weight of the crop oil concentrate, from about 2 to about 30 percent anionic surfactant; from 1 to about 20 percent fatty acid (b) (i) or from 10 to about 96 percent lower alkanol ester (b) (ii); and from 70 to about 10 percent hydrocarbon component. More preferably, the crop oil concentrate contains from 2 to 10 percent anionic surfactant; 4 to 10 percent fatty acid (b) (i) or from 10 to about 50 percent lower alkanol ester (b) (ii); and 88 to 40 percent hydrocarbon component. The hydrocarbon component is optional when the b) component is a fatty acid ester b)ii).

The crop oil concentrates of the subject invention may be utilized in many postemergent herbicide formulations, generally in amounts of from about 0.5 to about 8 L/ha, preferably from about 2 to about 5 L/ha. Many manufacturers recommend the use of crop oil concentrates for particular applications or, in some cases, for all applications of their herbicides. In other cases, the concentrates may be used as experience dictates. The crop oil concentrates of the subject invention have been found effective with herbicides of diverse chemical structure, for example with the cyclohexenone herbicides, with benzothiadiazinonedioxide herbicides, with the sulfonylurea and sulfonamide herbicides with diphenylether herbicides, with dipyridilium herbicides with imidazolinones, with N-phosphonoalkylglycines and with aryloxyphenoxy herbicides including analogues containing heterocycles, such as the quinoxalinyloxyphenoxy and from 88 to about 0 percent hydrocarbon component. More preferably, the crop oil concentrate contains from 2 to 10 percent anionic surfactant; 4 to 10 percent fatty acid (b) (i) or from 10 to about 50 percent lower alkanol ester (b) (ii); and 88 to 40 percent hydrocarbon component. The hydrocarbon component is optional when the b) component is a fatty acid ester b)ii). In these cases the lower alkanol ester (b)(ii) can comprise up to 96 percent of the crop oil concentrate.

The crop oil concentrates of the subject invention may be utilized in many postemergent herbicide formulations, generally in amounts of from about 0.5 to about 8 L/ha, preferably from about 2 to about 5 L/ha. Many manufacturers recommend the use of crop oil concentrates for particular applications or, in some cases, for all applications of their herbicides. In other cases, the concentrates may be used as experience dictates. The crop oil concentrates of the subject invention have been found effective with herbicides of diverse chemical structure, for example with the cyclohexenone herbicides, with benzothiadiazinonedioxide herbicides, with the sulfonylurea and sulfonamide herbicides with diphenylether herbicides, with dipyridilium herbicides with imidazolinones, with N-phosphonoalkylglycines and with aryloxyphenoxy herbicides including analogues containing heterocycles, such as the quinoxalinyloxyphenoxy herbicides. The crop oil concentrates are especially effective with the cyclohexenone-type herbicides, and particularly when these herbicides are used in conjunction with herbicides of other classes.

The cyclohexenone herbicides with which the subject invention crop oil concentrates may be used are well known. Examples of their preparation and use may be found in U.S. Pat. Nos. 3,950,420; 4,011,256, 4,249,937, and 4,666,510. Specific mention may be made of certain of the more common cyclohexenones, including alloxydim, sethoxydim, cycloxydim, clethodim, and cloproxydim.

The diphenyl ether herbicides and their analogues are likewise well known. These herbicides are described, for example, in chapter 14 of *Herbicides*, P. C. Kearney et al., published by Marcel Dekker, Inc., New York ©

1976. Many other classes of herbicides are also described in this two volume treatise. Also well known are the dipyridilium herbicides such as paraquat, diquat, and morfamquat.

In the examples which follow, herbicides or herbicide mixtures are tested for their efficacy against a variety of common weeds. In many cases, comparisons are made to similar compositions containing other crop oil concentrates. The "standard" crop oil concentrate used for comparison purposes is "Booster Plus E," a product of the Agway Corporation. This product has been widely used in herbicide applications and appears to have consistent formulation and product quality. In the examples, this "standard" crop oil concentrate is labeled "COC". In all the tables showing efficacy of the crop oil concentrate/herbicide mixtures against various species of weeds, the numerical values in the tables represent the percentage of weed control, or percent kill of the various species. The term "Concentrate" is used to represent "crop oil concentrate" in these tables.

In comparing the efficacy of the subject invention crop oil concentrates with alternative crop oil concentrates, the respective concentrates were added at levels of generally from 2 to 5 L/ha to tank mixes of the herbicides and agitated to prepare a uniform mixture.

Standard abbreviations for the various weed species found in the text which follows may be found below:

| | | |
|---|---|---|
| AVEFA | *Avena fatua* | wild oats |
| AVESA | *Avena sativa* | oats (volunteer) |
| BRAPP | *Brachiaria platyphylla* | broadleaf signal grass |
| BROSE | *Bromus secalinus* | cheat grass |
| CHEAL | *Chenopodium album* | common lambsquarters |
| DAOTE | *Daubentonia texana* | coffee weed |
| DATST | *Datura stramonium* | jimsonweed |
| DIGSA | *Digitoria sanguinalis* | large crabgrass |
| ECHCG | *Echinochloa crus-galli* | barnyard grass |
| FESAR | *Festuca arundinacea* | tall fescue |
| HORVU | *Hordeum vulgare* | barley (volunteer) |
| IPOLA | *Ipomoea lacunosa* | pitted morning glory |
| LEFFI | *Leptochloa filiformis* | red sprangletop |
| LOLMU | *Lolium multiflorum* | annual ryegrass |
| PANTE | *Panicum texanum* | texas panicum |
| POAAN | *Poa annua* | annual bluegrass |
| POAPR | *Poa pratensus* | perennial bluegrass |
| SETFA | *Setaria faberii* | giant foxtail |
| SETLU | *Setaria lutescens* | yellow foxtail |
| SETVI | *Setaria viridis* | green foxtail |
| SORHA | *Sorghum halepense* | Johnson grass |
| TRZAX | *Triticum aestivum* | wheat (volunteer) |
| XANPE | *Xanthium pennsylvanicum* | cocklebur |
| ZEAMX | *Zea mays* | corn (volunteer) |

Herbicide mixtures are frequently used in weed control. Often, one selective herbicide will show great efficacy in controlling several weed species but will have little effect on others. When complete weed control is desired either sequential application of two or more herbicides is required or one application of a mixture of two or more herbicides is required. Successive herbicide application is not cost-effective. However, the use of mixtures of herbicides often fails to achieve the desired results due to apparent antagonism between the herbicides.

Antagonism may be true biological antagonism where, for example, the biochemical effect of one herbicide is partially or wholly destroyed by the second herbicide. Antagonism may also be physical antagonism where either one herbicide or its formulation ingredients wholly or partially prevents the biological uptake of the second herbicide. It is frequently difficult, if not impossible, for the agriculturist to identify which of these types of antagonism is operative. Thus the term "apparent antagonism" is an appropriate one to describe the net, observable effect—a decrease in the efficacy of one herbicide when used in conjunction with another.

TABLE I

AMENDED
Weed Control with Sethoxydim

| Treatment Number | Additive Composition | | | | Bio-Response | | % Improvement Over COC, Composite | % Improvement Over DASH ®, Composite |
|---|---|---|---|---|---|---|---|---|
| | | | | | $GR_{50}$ | $GR_{80}$ | | |
| 1 | none | | | | 0.082 | 0.162 | −52% | −160 |
| 2 | COC[1] | | | | 0.052 | 0.108 | — | −70 |
| 3 | DASH ®[2] | | | | 0.037 | 0.057 | 41% | — |
| | KLEARFAC ® AA-270 | C-65 Methyl Esters | Oleic Acid | Aromatic ® 150 | | | | |
| 4 | 4 | 30 | 0 | 66 | 0.035 | 0.069 | 35% | −11 |
| 5 | 20 | 30 | 0 | 50 | 0.033 | 0.073 | 34% | −13 |
| 6 | 2 | 40 | 0 | 58 | 0.033 | 0.073 | 39% | −3 |
| 7 | 6 | 44 | 0 | 50 | 0.028 | 0.050 | 51% | 17 |
| 8 | 2 | 48 | 0 | 50 | 0.032 | 0.068 | 38% | −6 |
| 9 | 7.5 | 0 | 5 | 87.5 | — | — | 18%[3] | — |
| 10 | 10 | 40 | 0 | 50 | 0.026 | 0.057 | 48% | 12 |

[1]Proprietary composition, Booster Plus E
[2]Composition falling within the scope of U.S. application Ser. No. 104,658, now commonly owned U.S. Pat. No. 4,834,908.
[3]Estimated from side by side trials against DASH ® adjuvant

TABLE II

Weed Control with Sethoxydim

| Treatment Number | Additive Composition | | | | Bio-Response | | % Improvement Over COC, Composite | % Improvement Over DASH ®, Composite |
|---|---|---|---|---|---|---|---|---|
| | | | | | $GR_{20}$ | $GR_{30}$ | | |
| 11 | COC[1] | | | | 0.032 | 0.063 | — | −53% |
| 12 | DASH ®[2] | | | | 0.020 | 0.042 | 35% | — |
| | Anionic Surfactant | | C-65 Methyl Esters | Aromatic ® 150 | | | | |
| | Name | Amount | | | | | | |
| 13 | Crodafose ® Cap | 15 | 35 | 50 | 0.020 | 0.045 | 32% | −5% |

TABLE II-continued

Weed Control with Sethoxydim

| Treatment Number | Additive Composition | | | | Bio-Response GR$_{20}$ | GR$_{30}$ | % Improvement Over COC, Composite | % Improvement Over DASH ®, Composite |
|---|---|---|---|---|---|---|---|---|
| 14 | Surfine ® WNG-A | 15 | 35 | 50 | 0.017 | 0.040 | 40% | 8% |
| 15 | Alipal ® CO-436 | 20 | 30 | 50 | 0.020 | 0.038 | 39% | 6% |

[1]Proprietary composition, Booster Plus E
[2]Composition falling within the scope of U.S. application Ser. No. 104,658, now commonly owned U.S. Pat. No. 4,834,908.
[3]Estimated from side by side trials against DASH ® adjuvant Tables I and II indicate that weed control as measured by GR$_{50}$ and GR$_{80}$ values is significantly enhanced over the standard crop oil concentrate. The GR$_{50}$ and GR$_{80}$ values in Table I were calculated by log-probit regression based on observations made 13 days after treating on large crabgrass (DIGSA), green foxtail (SETVI), and corn (ZEAMX). These values represent the amount of herbicide needed to provide 50% and 80% control of the target weed species. The lower the value, the more effective the composition. Spray volume was 187 L/ha containing 4.7 L/ha of adjuvant except for treatment 2 which contained 2.3 L/ha.

The embodiments of the invention in which an exclusive privilege or property is claimed are defined as follows:

1. A crop oil concentrate, consisting essentially of, in parts by weight relative to the total formulation weight:
   a) from 2 to about 30 percent of an anionic surfactant selected from the group consisting of the partial sulfate and phosphate esters and carboxylates of monohydroxyl-functional polyoxyalkylene ethers, and their alkali metal, alkaline earth metal, and ammonium salts;
   b) one and only one of the following adjuvants:
      i) from 1 to about 20 percent of a fatty acid having from 10 to about 22 carbon atoms; and
      ii) from 10 to about 96 percent of a lower alkanol ester of a fatty acid having from 10 to about 22 carbon atoms; and
   c) a hydrocarbon component which is
      i) from 90 to about 10 percent of a hydrocarbon component when the adjuvant is b)i); and,
      ii) up to about 70 percent of a hydrocarbon component when the adjuvant is b)ii).

2. The composition of claim 1 wherein said fatty acid is selected from the group consisting of the unsaturated fatty acids having from 14 to 18 carbon atoms.

3. The composition of claim 1 wherein said lower alkanol ester of a fatty acid is selected from the methyl esters of myristic, palmitic, linoleic, linolenic, and oleic acids.

4. A crop oil concentrate, comprising, in weight percent based upon the total weight of the composition:
   a) from 2 to about 20 percent of an anionic surfactant selected from the group consisting of the partial sulfate and phosphate esters and carboxylates of monohydroxyl-functional polyoxyalkylene ethers and their alkali metal, alkaline earth metal, and ammonium salts;
   b) from 10 to about 50 percent of the methyl esters of fatty acids wherein said fatty acids are comprised predominantly of oleic and palmitic acids; and
   c) from 88 to about 40 percent of a hydrocarbon component, said crop oil concentrate being substantially free from C$_{10}$–C$_{22}$ fatty acids.

5. A crop oil concentrate, comprising, in weight percent based on the total weight of the composition:
   a) from 2 to about 20 percent of an anionic surfactant selected from the group consisting of the partial sulfate and phosphate esters and carboxylates of monohydroxyl-functional polyoxyalkylene ethers and their alkali metal, alkaline earth metal, and ammonium salts;
   b) from 1 to about 20 percent of a fatty acid having from 10 to about 22 carbons atoms; and
   c) from 90 to about 10 percent of a hydrocarbon component, said cop oil concentrate being substantially free from lower alkanol esters of C$_{10}$–C$_{22}$ fatty acids.

* * * * *